United States Patent
Suzuki et al.

(10) Patent No.: US 10,605,780 B2
(45) Date of Patent: Mar. 31, 2020

(54) ROAD SURFACE CONDITION ESTIMATION DEVICE

(71) Applicant: DENSO CORPORATION, Kariya, Aichi-pref. (JP)

(72) Inventors: Youichirou Suzuki, Nisshin (JP); Akira Takaoka, Nisshin (JP); Takatoshi Sekizawa, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 72 days.

(21) Appl. No.: 15/770,828

(22) PCT Filed: Sep. 23, 2016

(86) PCT No.: PCT/JP2016/078022
§ 371 (c)(1),
(2) Date: Apr. 25, 2018

(87) PCT Pub. No.: WO2017/073211
PCT Pub. Date: May 4, 2017

(65) Prior Publication Data
US 2018/0364197 A1 Dec. 20, 2018

(30) Foreign Application Priority Data
Oct. 27, 2015 (JP) .................................. 2015-210985

(51) Int. Cl.
*G01N 29/04* (2006.01)
*B60T 8/173* (2006.01)
(Continued)

(52) U.S. Cl.
CPC ........... *G01N 29/041* (2013.01); *B60C 19/00* (2013.01); *B60C 23/06* (2013.01); *B60C 99/00* (2013.01);
(Continued)

(58) Field of Classification Search
CPC ................. G01N 29/041; G01N 29/44; G01N 2291/263; B60T 8/173; B60T 8/1725;
(Continued)

(56) References Cited

U.S. PATENT DOCUMENTS

| | | |
|---|---|---|
| 2008/0125948 A1 | 5/2008 | Matsuda et al. |
| 2009/0302560 A1 | 12/2009 | Koguchi |
| 2010/0024538 A1* | 2/2010 | Hammerschmidt .. B60C 23/064 73/146 |
| 2010/0063671 A1 | 3/2010 | Fink et al. |

(Continued)

FOREIGN PATENT DOCUMENTS

| | | |
|---|---|---|
| JP | 2008126942 A | 6/2008 |
| JP | 2009292283 A | 12/2009 |

(Continued)

*Primary Examiner* — Daniel S Larkin
*Assistant Examiner* — Anthony W Megna Fuentes
(74) *Attorney, Agent, or Firm* — Harness, Dickey & Pierce, P.L.C.

(57) ABSTRACT

In order to detect a road surface condition, a road surface condition estimation device extracts a detection signal of a portion that detects vibration in a tire tangential direction in a vibration detection and power generation unit which is in a ground contact section, for example, a vibration power generation element. In this case, it is identified that the vibration detection and power generation unit is in the ground contact section, based on whether a centrifugal force acting on the vibration detection and power generation unit is generated, or not, and it is identified that a time when no centrifugal force is generated is in the ground contact section. As a result, even if a pulse level of an output voltage of the vibration detection generation unit changes according to a traveling speed of the vehicle, the ground contact section can be accurately identified.

2 Claims, 12 Drawing Sheets

(51) Int. Cl.
*G01H 1/00* (2006.01)
*B60T 8/172* (2006.01)
*B60C 99/00* (2006.01)
*B60W 40/068* (2012.01)
*B60C 23/06* (2006.01)
*G01N 29/44* (2006.01)
*B60C 19/00* (2006.01)

(52) U.S. Cl.
CPC ............ *B60T 8/173* (2013.01); *B60T 8/1725* (2013.01); *B60W 40/068* (2013.01); *G01H 1/003* (2013.01); *G01N 29/44* (2013.01); *B60C 2019/004* (2013.01); *B60T 2210/12* (2013.01); *G01N 2291/263* (2013.01)

(58) Field of Classification Search
CPC ..... B60T 2210/12; G01H 1/003; B60C 99/00; B60C 23/06; B60C 19/00; B60C 2019/004; B60W 40/068
See application file for complete search history.

(56) References Cited

U.S. PATENT DOCUMENTS

| | | | |
|---|---|---|---|
| 2011/0282548 A1* | 11/2011 | Haas | B60T 8/1725 701/36 |
| 2013/0116972 A1 | 5/2013 | Hanatsuka et al. | |
| 2014/0150543 A1* | 6/2014 | Shima | B60C 23/0416 73/146 |
| 2014/0343797 A1* | 11/2014 | Naito | B60W 50/0098 701/45 |
| 2016/0368501 A1 | 12/2016 | Suzuki et al. | |
| 2016/0368502 A1 | 12/2016 | Suzuki et al. | |

FOREIGN PATENT DOCUMENTS

| | | |
|---|---|---|
| JP | 2010066261 A | 3/2010 |
| JP | 2011242303 A | 12/2011 |
| JP | 2015174637 A | 10/2015 |
| JP | 2015174638 A | 10/2015 |
| WO | WO-2017073210 A1 | 5/2017 |

* cited by examiner

GROUND CONTACT LENGTH

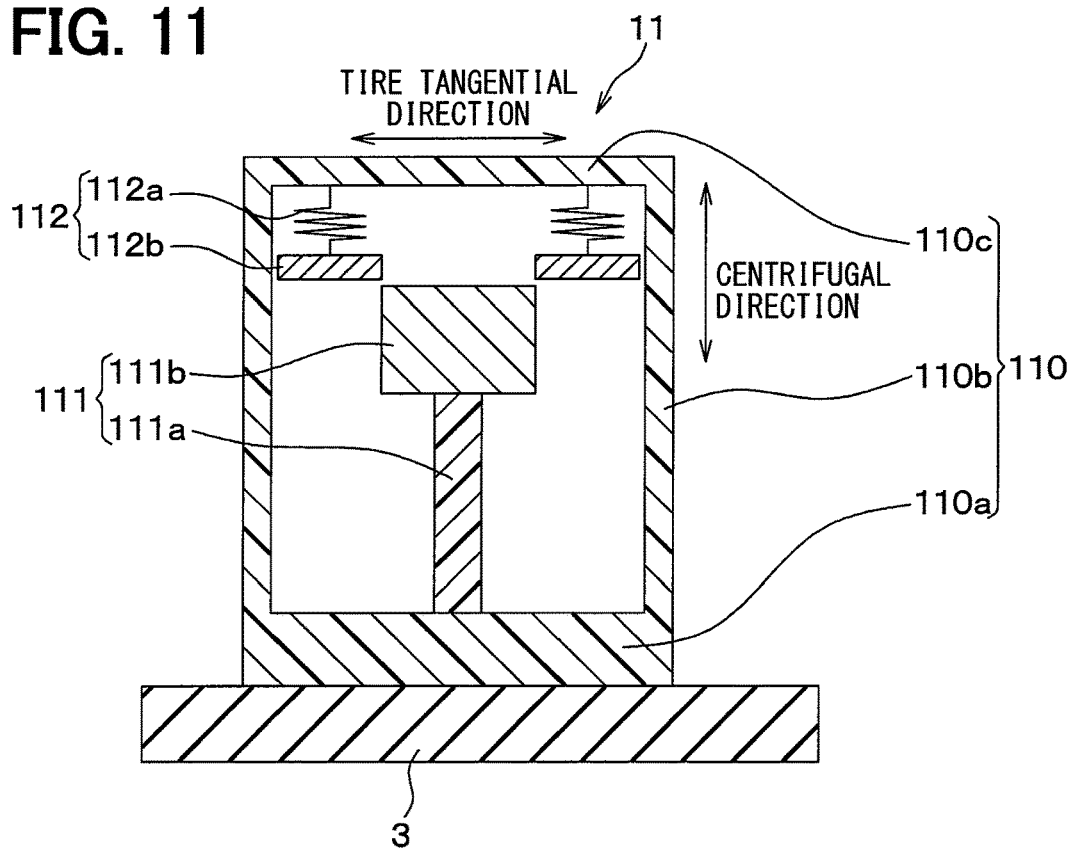
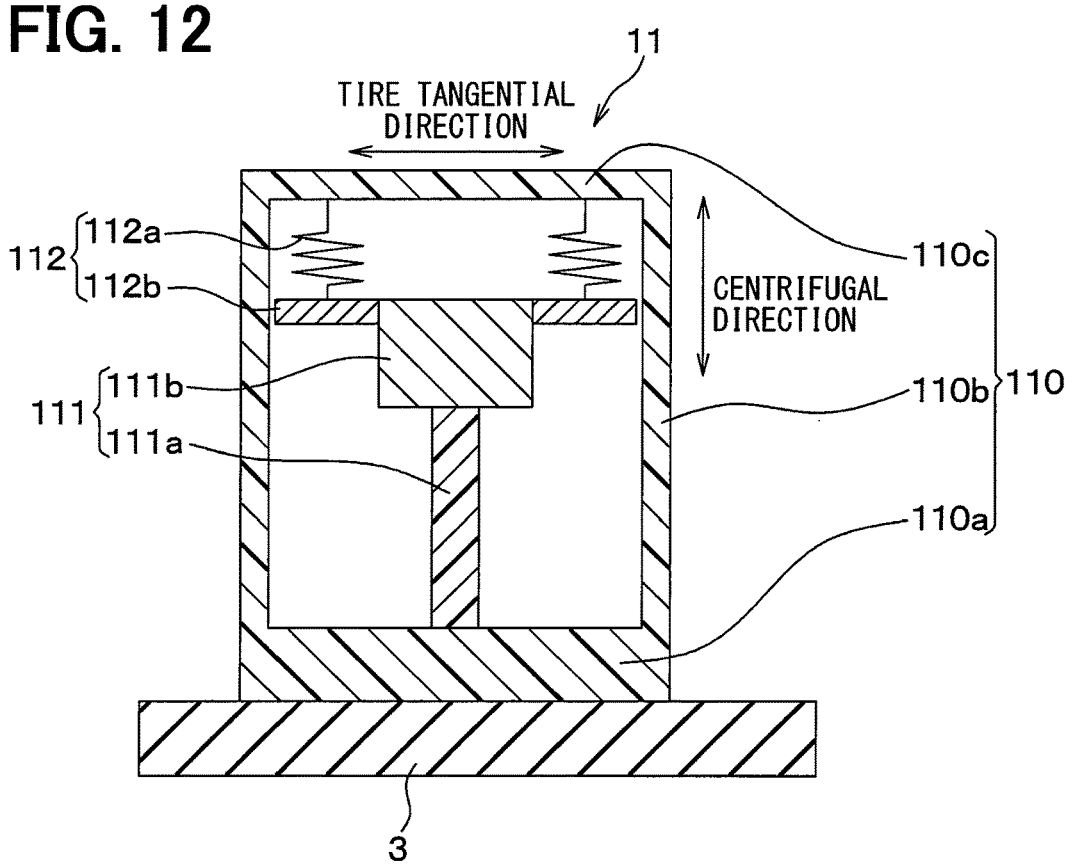

ROAD SURFACE CONDITION ESTIMATION DEVICE

CROSS REFERENCE TO RELATED APPLICATIONS

This application is a U.S. National Phase Application under 35 U.S.C. 371 of International Application No. PCT/JP2016/078022 filed on Sep. 23, 2016 and published in Japanese as WO 2017/073211 A1 on May 4, 2017. This application is based on and claims the benefit of priority from Japanese Patent Application No. 2015-210985 filed on Oct. 27, 2015. The entire disclosures of all of the above applications are incorporated herein by reference.

TECHNICAL FIELD

The present disclosure relates to a road surface condition estimation device that estimates a road surface condition based on vibrations to which tires are subjected.

BACKGROUND ART

Up to now, a technique in which an acceleration sensor is buried in a back surface of a tire tread, and a road surface condition, for example, a condition of an asphalt road, a snowy road, or an frozen road, is estimated based on a detection signal of the acceleration sensor has been proposed (for example, refer to Patent Literature 1). Specifically, in the case where the acceleration sensor is buried in the back surface of the tire tread, when a portion of the tire tread corresponding to a placement location in which the acceleration sensor is disposed contacts a road surface in association with the rotation of the tire, a vibration component corresponding to the road surface condition is superimposed on a detection signal of the acceleration sensor. For that reason, up to now, a frequency component of the vibration in a ground contact section where the portion of the tire tread corresponding to the placement location of the acceleration sensor contacts the road surface is analyzed to estimate the road surface condition.

PRIOR ART LITERATURES

Patent Literature

Patent Literature 1: JP 2011-242303 A

SUMMARY OF INVENTION

A level (hereinafter referred to as "pulse level") of a pulse waveform of the vibration detected by the acceleration sensor greatly varies depending on a traveling speed. For that reason, the ground contact section in which the portion of the tire tread corresponding to the placement location of the acceleration sensor contacts the road surface is not determined based on the pulse level with high precision, and the estimation of the road surface condition cannot be performed accurately.

The present disclosure aims at providing a road surface condition estimation device capable of accurately identifying a ground contact section where a portion of a tire tread corresponding to a location of a vibration detection unit for detecting vibration of the tire is in contact with a road surface.

According to a first aspect of the present disclosure, a road surface condition estimation device includes a tire side device and a vehicle side device. The tire side device includes a vibration detection unit which is attached to a rear surface of a tread of a tire provided in the vehicle and which includes a portion that detects vibration in a tangential direction of the tire and a portion that detects a centrifugal force, the vibration detection unit configured to output a first detection signal corresponding to a magnitude of the vibration in the tangential direction and a second detection signal corresponding to the centrifugal force, a signal processing unit which includes a section identification unit which identifies a ground contact section in which a portion of the tread corresponding to a placement location of the vibration detection unit contacts the road during one rotation of the tire, and a level calculation unit which calculates a level of a high frequency component of the first detection signal in the ground contact section, and a transmitter which transmits a calculation result of the level of the high frequency component as road surface condition data representing a road surface condition. The vehicle side device includes a receiver which receives the road surface condition data transmitted from the transmitter, and a condition estimation unit which estimates a road surface condition of a traveling road surface of the tire based on the road surface condition data. Further, in the tire side device, the section identification unit includes a centrifugal force detection unit that detects a centrifugal force acting on the vibration detection unit based on the second detection signal, and identifies the ground contact section according to the centrifugal force detected by the centrifugal force detection unit.

In this way, in order to detect the road surface condition, the first detection signal of the portion of the vibration detection unit that is in the ground contact section for detecting the vibration in the tire tangential direction is extracted. Then, it is identified that the vibration detection portion is in the ground contact section at that time based on whether the centrifugal force acting on the vibration detection unit is generated, or not. As a result, even if the pulse level of the first detection signal of the vibration detection unit changes according to the traveling speed of the vehicle, the ground contact section can be accurately identified. Therefore, the road surface condition can be accurately detected based on the ground contact section identified with high accuracy.

Further, according to a road surface condition estimation device of a second aspect of the present disclosure, the tire side device includes a vibration detection unit which is attached to a rear surface of a tread of a tire provided in the vehicle and which includes a portion detecting vibration in a tangential direction of the tire and a portion detecting a centrifugal force, the vibration detection unit configured to output a detection signal corresponding to a magnitude of the vibration in the tangential direction, a signal processing unit which includes a level calculation unit which calculates a level of a high frequency component of the detection signal, and a transmitter which transmits a calculation result of the level of the high frequency component as road surface condition data representing a road surface condition. Further, the vehicle side device includes a receiver which receives the road surface condition data transmitted from the transmitter, and a condition estimation unit that estimates a road surface condition of a traveling road surface of the tire based on the road surface condition data. Further, the vibration detection unit is configured to not detect vibration in the tangential direction of the tire when the portion detecting the centrifugal force detects that the centrifugal force acts, and is configured to detect vibration in the tangential direction of the tire only when the portion detecting the centrifugal force detects that no centrifugal force acts.

With the use of the vibration detection unit described above, the detection signal of the vibration detection unit can be transmitted to the level calculation unit in the signal processing unit only while the vibration detection unit is in the ground contact section. Therefore, the structure of the vibration detection unit can have the functions of the centrifugal force detection unit and the switch unit. Even with the configuration described above, the same advantages as those of the road surface condition estimation device according to the first aspect described above can be obtained. Further, there is no need to provide the section identification unit including the centrifugal force detection unit and the like in the signal processing unit. This makes it possible to reduce a processing load of the portion of the signal processing unit which is implemented by a microcomputer, and also makes it possible to reduce power consumption.

BRIEF DESCRIPTION OF DRAWINGS

FIG. 11 is a cross-sectional view showing a state in which a centrifugal force of a vibration detection and power generation unit is not exerted according to the third embodiment.

FIG. 12 is a cross-sectional view showing a state in which a centrifugal force of the vibration detection and power generation unit shown in FIG. 11 is exerted.

DESCRIPTION OF EMBODIMENTS

Embodiments of the present disclosure will be described below with reference to the accompanying drawings. In the following respective embodiments, parts identical with or equivalent to each other are denoted by the same symbols for description.

First Embodiment

A road surface condition estimation device according to the present embodiment will be described with reference to FIGS. 1 to 8. The road surface condition estimation device according to the present embodiment is used to estimate a road surface condition during traveling based on vibration on a ground contact surface of a tire provided in each wheel of a vehicle.

Figure 1:
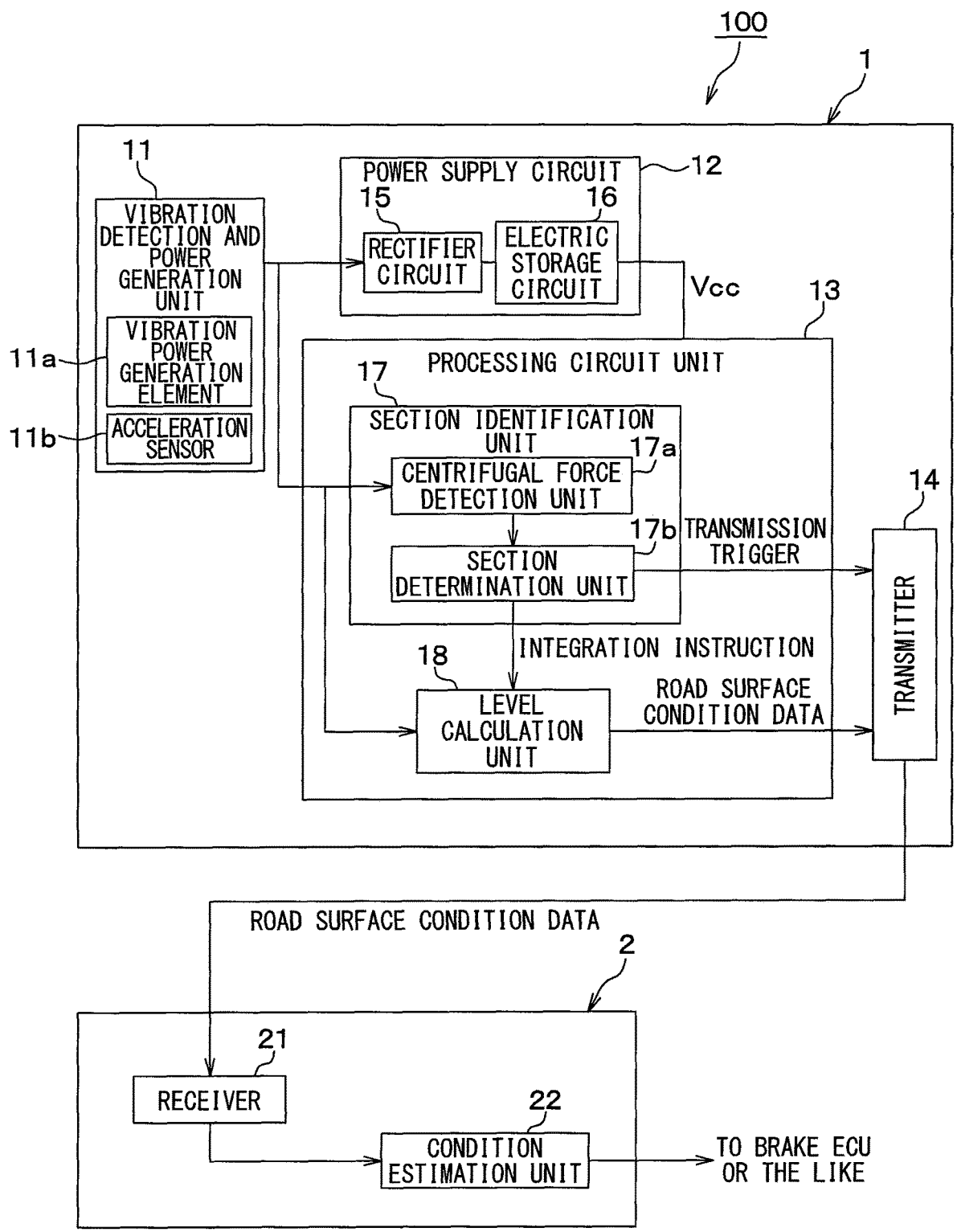
FIG. 1 is a diagram illustrating an overall block configuration of a road surface condition estimation device according to a first embodiment.

As illustrated in FIG. 1, a road surface condition estimation device 100 includes a tire side device 1 provided on a tire side and a vehicle side device 2 provided on a vehicle body side. The road surface condition estimation device 100 transmits data indicative of a road surface condition during traveling from the tire side device 1, the vehicle side device 2 receives the data transmitted from the tire side device 1, and estimates the road surface condition during traveling based on the data. Specifically, the tire side device 1 and the vehicle side device 2 are configured as follows.

Figure 2:
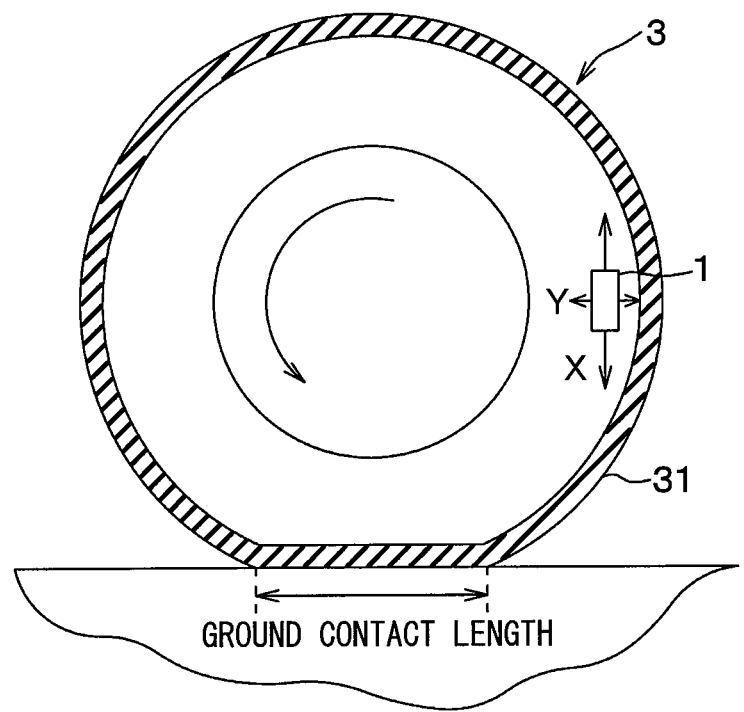
FIG. 2 is a schematic cross-sectional view of a tire to which a tire side device is attached.

As illustrated in FIG. 1, the tire side device 1 includes a vibration detection and power generation unit 11, a power supply circuit 12, a processing circuit unit 13, and a transmitter 14. As illustrated in FIG. 2, the tire side device 1 is disposed on a back surface side of a tread 31 of a tire 3.

The vibration detection and power generation unit 11 includes a biaxial sensor or the like capable of detecting biaxial vibration and forms a vibration detection unit. Specifically, the vibration detection and power generation unit 11 detects vibration in a direction in contact with a circular orbit drawn by the tire side device 1 when the tire 3 rotates, that is, in a tire tangential direction which is a direction of an arrow X in FIG. 2, as one of the two axes. The vibration detection and power generation unit 11 outputs a detection signal corresponding to a first detection signal according to the detected vibration. In addition, the vibration detection and power generation unit 11 detects a centrifugal force acting on the vibration detection generation unit 11 when the tire 3 rotates, in other words, a force acting in a centrifugal direction of the tire which is a direction indicated by an arrow Y in FIG. 2, as the other of the two axes. In the case of the present embodiment, the vibration detection and power generation unit 11 detects the vibration in the tire centrifugal direction to output a detection signal as a second detection signal corresponding to the centrifugal force.

Further, in the present embodiment, the vibration detection and power generation unit 11 outputs the detection signal corresponding to the vibration in the tire tangential direction, and additionally converts a vibration energy into an electric energy, and generates a power supply of the tire side device 1 based on the converted electric energy. For example, the vibration detection and power generation unit 11 is configured to have a vibration power generation element 11a. The vibration power generation element 11a is disposed to generate a power due to the vibration in the tire tangential direction. For example, an electrostatic induction power generation element (for example, electret), a piezoelectric element, a friction element, a magnetostrictive element, or an electromagnetic induction element can be applied as the vibration power generation element 11a of the above type. If only the detection signal corresponding to the vibration in the tire tangential direction is output without considering an intended purpose for power generation, others, for example, an acceleration sensor can be used as the vibration power generation element 11a.

For example, in the case where the electrostatic induction power generation element is used as the vibration power generation element 11a, when an upper electrode to be positively charged by electrostatic induction vibrates in a horizontal direction with respect to a lower electrode having negative charges, static charges caused by the electrostatic induction are varied, and an electromotive force is produced to generate a power. The power supply of the tire side device 1 is generated based on the power generation of the vibration power generation element 11a, and the detection signal corresponding to the magnitude of vibration in the tire tangential direction is generated.

In other words, when the vehicle having the road surface condition estimation device 100 travels, the tread 31 of the tire 3 vibrates due to various factors such as a rotational movement of the tire 3 and unevenness of a road surface. When the vibration is transmitted to the vibration power generation element 11a, the power is generated by the vibration power generation element 11a, and transmitted to the power supply circuit 12 to generate the power supply of the tire side device 1. Since an output voltage when the vibration power generation element 11a generates the power is changed according to the magnitude of vibration, the output voltage of the vibration power generation element 11a is transmitted to the processing circuit unit 13 as a detection signal indicative of the magnitude of vibration in the tire tangential direction. The output voltage of the vibration power generation element 11a is an AC voltage since the upper electrode reciprocates due to the vibration.

In addition, the vibration detection and power generation unit 11 according to the present embodiment is configured to include an acceleration sensor 11b that detects vibration in the tire centrifugal direction in order to detect the centrifugal force acting on the vibration detection and power generation unit 11. The acceleration sensor 11b outputs a detection signal corresponding to the centrifugal force acting on the vibration detection and power generation unit 11. Although the acceleration sensor 11 b is taken as an example in this case, another element such as a piezoelectric element may be applied as long as the element can detect the centrifugal force acting on the vibration detection and power generation unit 11.

The power supply circuit 12 stores electricity based on the output voltage of the vibration detection and power generation unit 11 to generate a power supply, and supplies a power to the processing circuit unit 13 and the transmitter 14. The power supply circuit 12 is configured to include a rectifier circuit 15 and an electric storage circuit 16.

The rectifier circuit 15 is a known circuit that converts the output voltage of the vibration detection and power generation unit 11, for example, an AC voltage output from the vibration power generation element 11a into a DC voltage. The AC voltage output by the vibration power generation element 11a is converted into the DC voltage by the rectifier circuit 15, and output to the electric storage circuit 16. The rectifier circuit 15 may be implemented as a full-wave rectifier circuit or a half-wave rectifier circuit.

The electric storage circuit 16 stores the DC voltage applied from the rectifier circuit 15, and is implemented as a capacitor. The output voltage of the vibration detection and power generation unit 11 is stored in the electric storage circuit 16 through the rectifier circuit 15, and with the stored voltage as a power supply, the power is supplied to the processing circuit unit 13 or the transmitter 14 provided in the tire side device 1. With the provision of the electric storage circuit 16 in the power supply circuit 12, when the vibration detection and power generation unit 11 excessively generate the power, the electric storage circuit 16 stores an excessive power, and when the amount of power generation is insufficient, the power supply circuit 12 compensates the insufficient power.

The processing circuit unit 13 is a portion corresponding to a signal processing unit. Since the high frequency component included in a detection signal of the vibration in the tire tangential direction from the vibration detection and power generation unit 11 represents the road surface condition, the processing circuit unit 13 processes the detection signal to obtain data representing the road surface condition and transmits the data to the transmitter 14.

Specifically, the processing circuit unit 13 captures a detection signal in the tire tangential direction indicated by the vibration power generation element 11a, based on a detection signal corresponding to the centrifugal force from the acceleration sensor 11b. That is, the processing circuit unit 13 detects the ground contact section based on the centrifugal force acting on the vibration detection and power generation unit 11, and captures the output voltage indicated by the detection signal in the tire tangential direction from the vibration detection and power generation section 11 which is in the ground contact section. The term "ground contact section" as used in the present specification means a section where a portion of the tread 31 of the tire 3 corresponding to the placement location of the vibration detection and power generation unit 11 contacts the road surface. The ground contact section can be identified by detecting the centrifugal force by the vibration detection and power generation unit 11. In other words, since the tire 3 rotates in a road noncontact section which is not in the ground contact section, a centrifugal force corresponding to the tire rotational speed is applied to the vibration detection and power generation unit 11. However, since a motion of the tire 3 changes to a linear motion during the ground contact section, no centrifugal force acts on the vibration detection and power generation unit 11. For that reason, the centrifugal force is detected by the vibration detection and power generation unit 11, and a time when no centrifugal force acts is identified as the ground contact section. As a result, the ground contact section can be accurately identified corresponding to the traveling speed.

In the ground contact section, the high frequency component included in the detection signal in the tire tangential direction of the tire indicated by the vibration power generation element 11a represents the road surface condition. For that reason, the processing circuit unit 13 extracts the high frequency component, generates data representing the road surface condition based on the extracted high frequency component, and transmits the generated data to the transmitter 14.

More specifically, the processing circuit unit 13 is a well-known microcomputer having various circuits, a CPU, a ROM, a RAM, an I/O, and so on, and performs the above process based on the detection signal of the vibration in the tire tangential direction of the tire and the detection signal corresponding to the centrifugal force in the vibration detection and power generation unit 11. The processing circuit unit 13 includes, as portions for performing those processing, a section identification unit 17 and a level calculation unit 18.

The section identification unit 17 performs functions of identifying the ground contact section and notifying the level calculation unit 18 that the vibration power generation element 11 is in the ground contact section. The section identification unit 17 has a centrifugal force detection unit 17a and a section determination unit 17b.

The centrifugal force detection unit 17a receives a detection signal corresponding to the centrifugal force from the vibration detection and power generation unit 11 and detects the centrifugal force acting on the vibration detection and power generation unit 11. For example, in the case where the portion detecting the centrifugal force in the vibration detection and power generation unit 11 is the acceleration sensor 11b, the centrifugal force detection unit 17a receives the detection signal of the acceleration sensor 11b, and detects the centrifugal force acting on the vibration detection and power generation portion 11 based on the received detection signal.

The section determination unit 17b determines that the vibration detection and power generation portion 11 is in the ground contact section based on the detection result of the centrifugal force detection unit 17a. If the section determination unit 17b determines that the vibration detection and power generation portion 11 is in the ground contact section, the section determination unit 17b transmits the determination result to the level calculation unit 18, and issues an instruction to rectify and integrate the high frequency components included in the output voltage of the vibration power generation element 11a during the ground contact section.

Figure 3A:
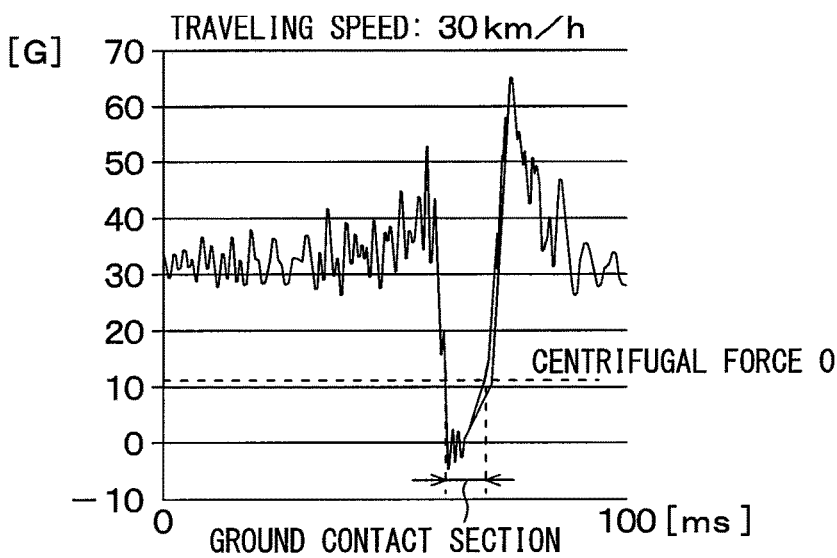
FIG. 3(a) is a graph showing a waveform of an acceleration in a tire centrifugal direction which is applied to a vibration detection and power generation unit when a traveling speed is 30 km/h.
Figure 3B:
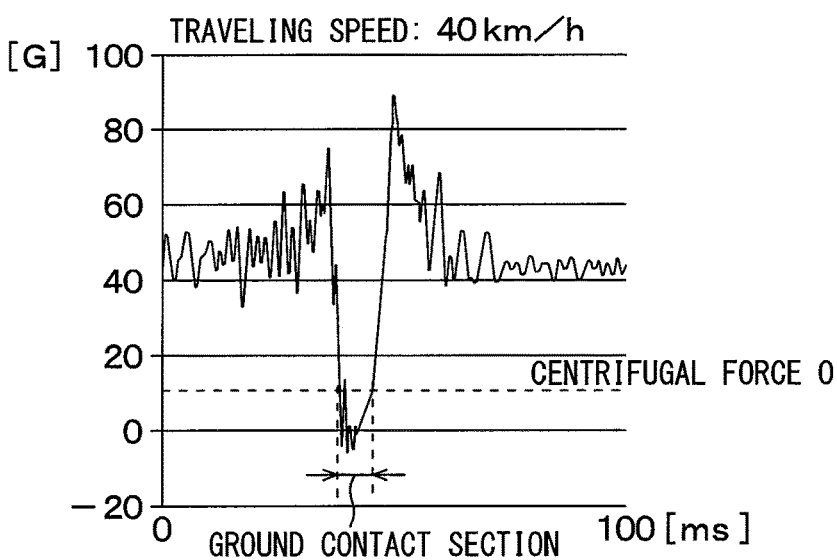
FIG. 3(b) is a graph showing a waveform of the acceleration in the tire centrifugal direction which is applied to the vibration detection and power generation unit when the traveling speed is 40 km/h.
Figure 3C:
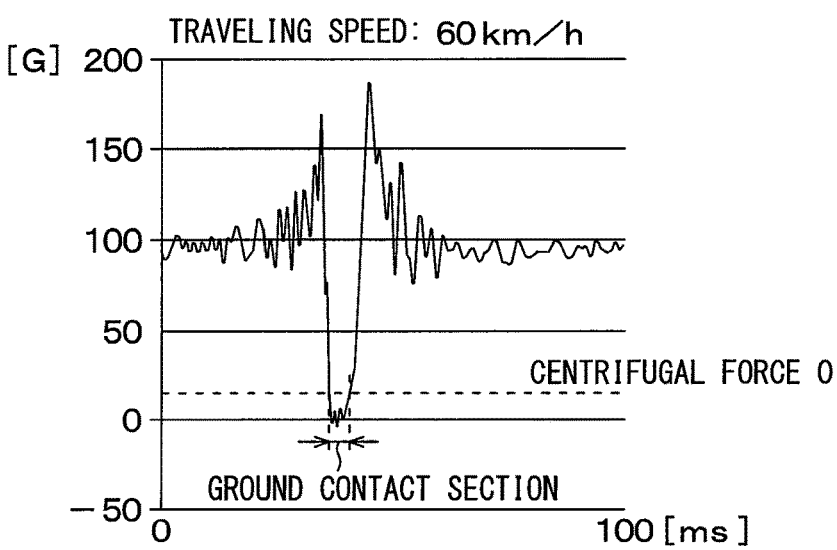
FIG. 3(c) is a graph showing a waveform of the acceleration in the tire centrifugal direction which is applied to the vibration detection and power generation unit when the traveling speed is 60 km/h.

Specifically, the section determination unit 17b determines that a period during which the centrifugal force detection unit 17a detects that the centrifugal force does not act on the vibration detection and power generation unit 11, that is, a period during which the centrifugal force is 0 is in the ground contact section. For example, in the case where the portion detecting the centrifugal force in the vibration detection and power generation unit 11 is the acceleration sensor 11b, an acceleration indicated by the detection signal of the acceleration sensor 11b has waveforms shown in FIGS. 3(a) to 3(c). FIGS. 3(a) to 3(c) show results of examining the detection signal of the acceleration sensor while changing the traveling speed of the vehicle. However, even if the traveling speed of the vehicle is changed, the centrifugal force becomes 0 in the ground contact section, and it is found that no centrifugal force acts on the vibration detection and power generation unit 11. For that reason, the section determination unit 17b detects that the centrifugal force does not act on the vibration detection and power generation unit 11 based on the detection signal of the acceleration sensor 11b, determines that such a time is in the ground contact section, and transmits the determination result to the level calculation unit 18. For example, when the centrifugal force is equal to or less than a threshold, for example, equal to or lower than 0, the section determination unit 17b can detect that the centrifugal force does not act on the vibration detection and power generation portion 11.

The section determination unit 17b causes the transmitter 14 to generate a transmission trigger for transmitting a calculation result of the level calculation unit 18 to the vehicle side device 2 as road surface condition data indicative of the road surface condition.

Figure 4:
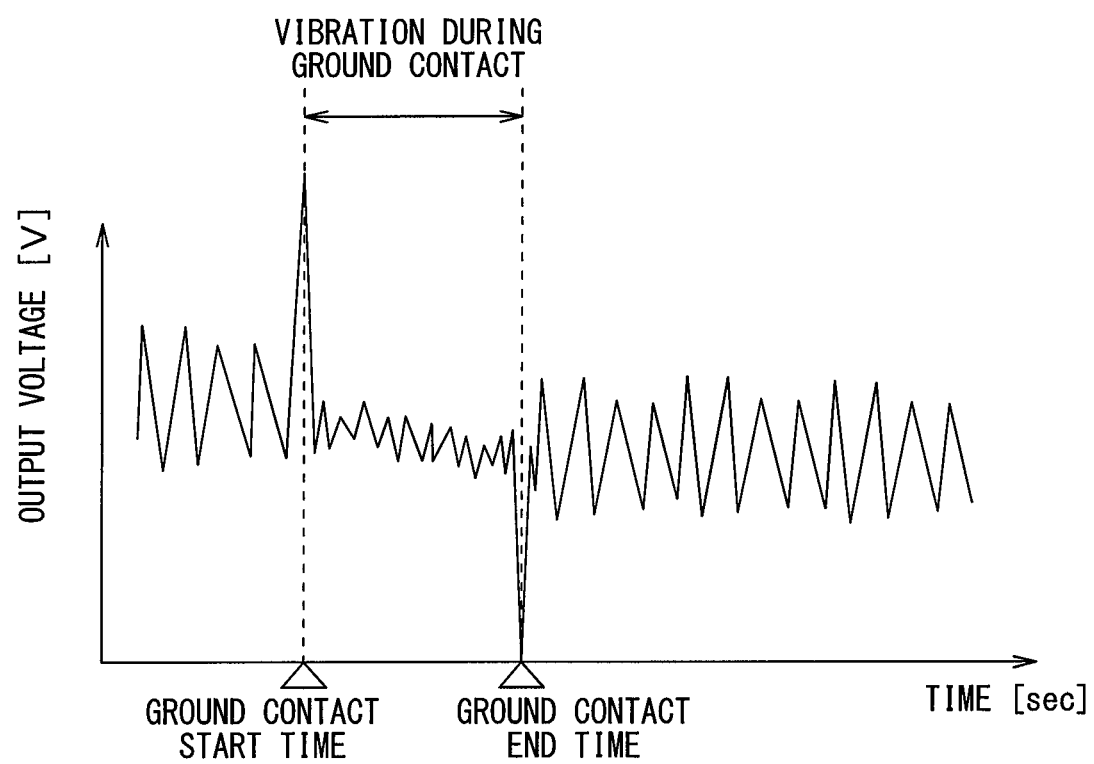
FIG. 4 is an output voltage waveform diagram of a vibration power generation element during tire rotation.

In this situation, an output voltage waveform of the vibration power generation element 11a during tire rotation is, for example, illustrated in FIG. 4. As illustrated in the figure, the output voltage of the vibration power generation element 11a reaches a local maximum value at a ground contact start time when a portion of the tread 31 corresponding to the placement location of the vibration detection and power generation unit 11 starts to contact the road in association with the rotation of the tire 3. Further, as illustrated in FIG. 4, the output voltage of the vibration power generation element 11a reaches a local minimum value at a ground contact end time when changing from a state in which the portion of the tread 31 corresponding to the placement position of the vibration detection and power generation unit 11 contacts the ground to a state in which the portion no longer contacts the road in association with the rotation of the tire 3.

Alternatively, the output voltage of the vibration power generation element 11a may be compared with a threshold, to detect a timing of taking the local maximum value and a timing of taking the local minimum value, thereby being capable of determining the ground contact section. However, since the output voltage of the vibration power generation element 11a largely varies according to the traveling speed of the vehicle, the ground contact section cannot be determined with high accuracy.

For that reason, the section determination unit 17b accurately determines that the vibration detection and power generation portion 11 is in the ground contact section based on the detection result of the centrifugal force detection unit 17a.

Further, a timing at which a state where the centrifugal force acting on the vibration detection and power generation unit 11 is 0 switches to a state where the centrifugal force is generated based on the detection result of the centrifugal force detection unit 17a is the ground contact end time of the vibration detection and power generation unit 11. Therefore, the section determination unit 17b transmits a transmission trigger to the transmitter 14 at this timing. As a result, the transmitter 14 transmits the calculation result transmitted from the level calculation unit 18 as the road surface condition data. As described above, because the data transmission by the transmitter 14 is not always performed, but is performed exclusively at the ground contact end time of the vibration detection and power generation unit 11, the power consumption can be reduced.

Upon receiving the fact that the vibration detection and power generation portion 11 is in the ground contact section from the section determination unit 17b, the level calculation unit 18 calculates the level of the high frequency component caused by the vibration of the tire 3 included in the detection signal of the portion detecting the vibration in the tire tangential direction in the vibration detection and power generation unit 11 during that period. The level calculation unit 18 transmits the calculation result to the transmitter 14 as road surface condition data indicative of the road surface condition. The level calculation unit 18 calculates the level of the high frequency component as an index indicative of the road surface condition, and its reason will be described with reference to FIGS. 5 and 6. In the following description, a case where the portion detecting the vibration in the tire tangential direction in the vibration detection and power generation unit 11 is the vibration power generation element 11a will be described as an example.

Figure 5A:
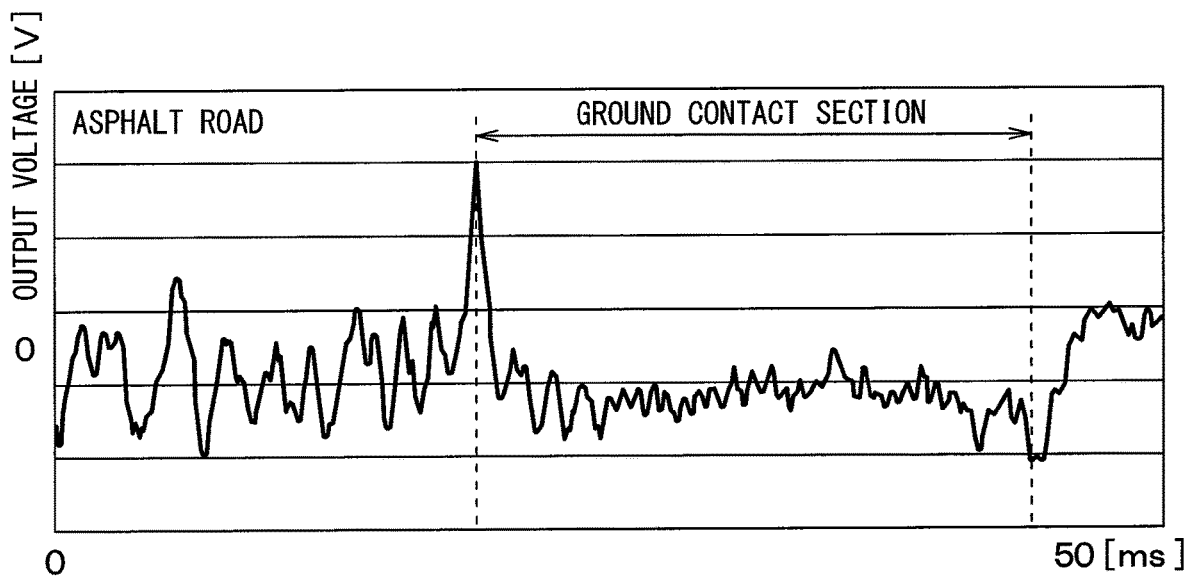
FIG. 5(a) is a graph showing a change in output voltage of the vibration power generation element when traveling on a high μ road surface whose road surface friction coefficient (hereinafter referred to as μ) is relatively large such as an asphalt road.
Figure 5B:
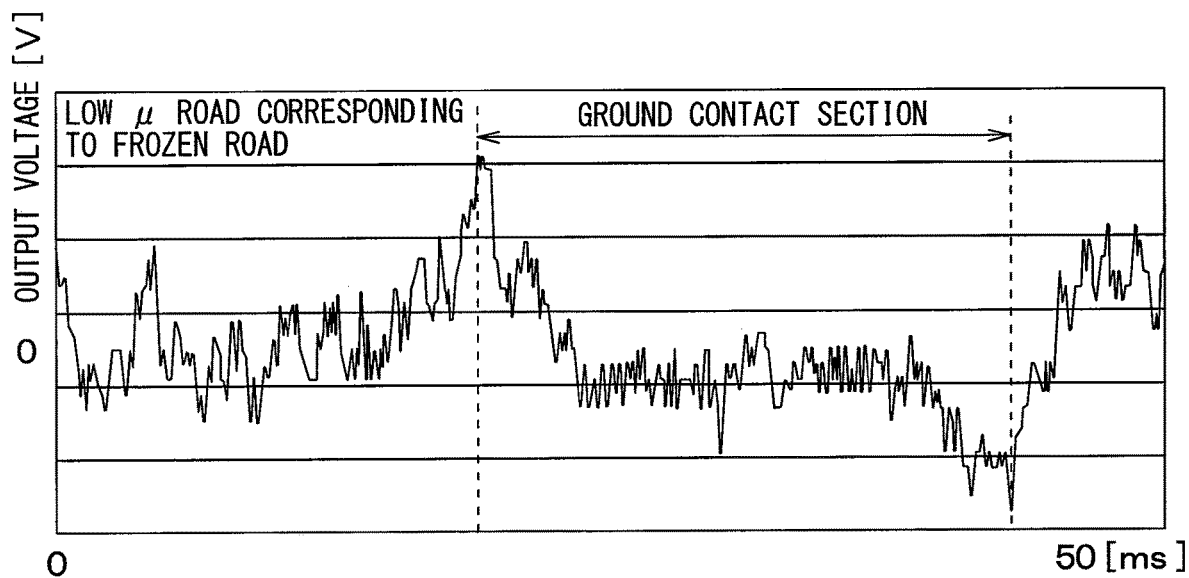
FIG. 5(b) is a graph showing a change in the output voltage of the vibration power generation element when traveling on a low μ road surface whose road surface μ is relatively small such as a frozen road.

FIG. 5(a) shows a change in output voltage of the vibration power generation element 11a when traveling on a high μ road surface whose road surface μ is relatively large such as an asphalt road. FIG. 5(b) shows a change in the output voltage of the vibration power generation element 11a when traveling on a low μ road surface whose road surface μ is relatively small such as a frozen road.

Figure 6:
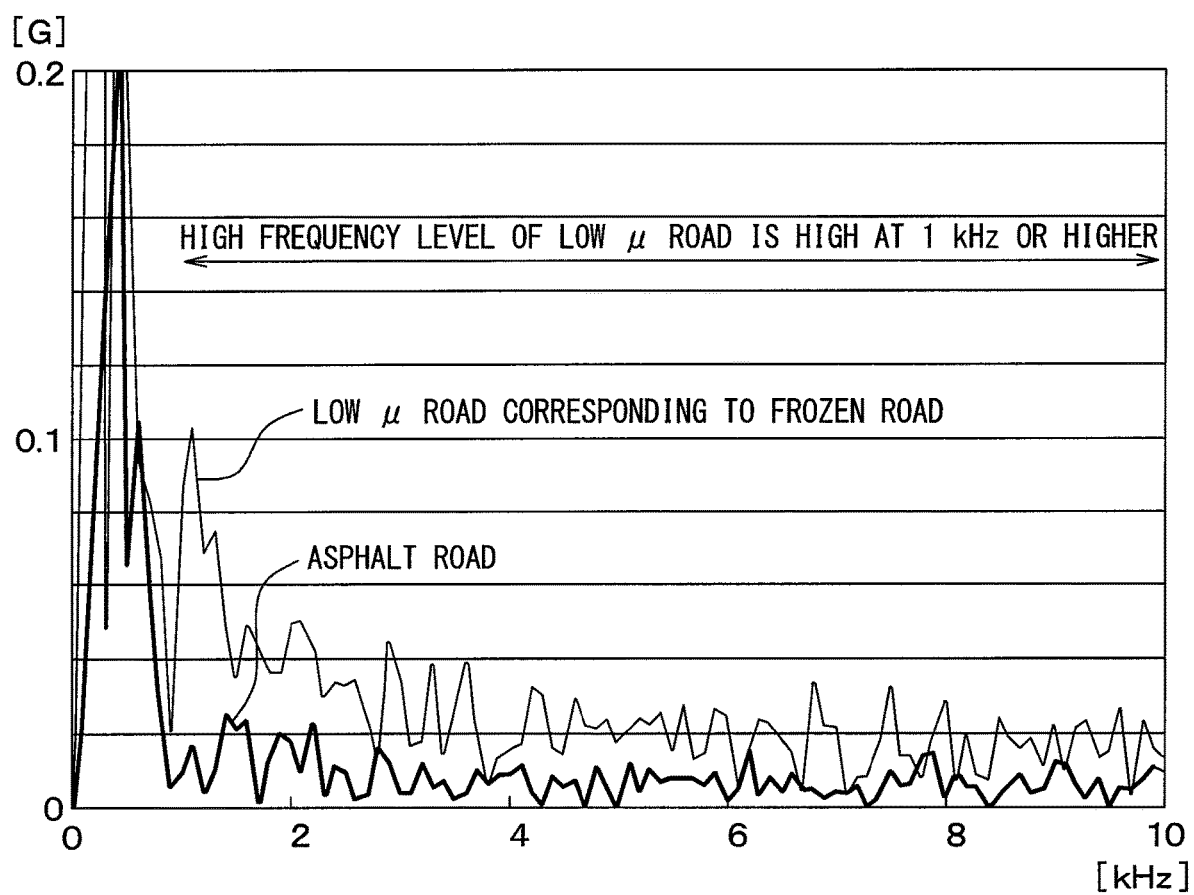
FIG. 6 is a graph showing results of performing a frequency analysis of the output voltage in a ground contact section in each of the case of traveling on the high μ road surface and the case of traveling on the low μ road surface.

As can be seen from those figures, regardless of the road surface μ, the output voltage of the vibration power generation element 11a becomes the local maximum value and the local minimum value at the beginning and the last of the ground contact section, that is, at a ground contact start time and a ground contact end time of the vibration detection and power generation unit 11. However, fine high frequency vibration caused by slip of the tire 3 is superimposed on the output voltage when the vehicle travels on the low μ road surface due to an influence of the road surface μ. For that reason, in each of the case of traveling on the high μ road surface and the case of traveling on the low μ road surface, when the frequency analysis of the output voltage in the ground contact section is performed, results illustrated in FIG. 6 are obtained. In other words, in a low frequency band, a high level is obtained when traveling on each of the high μ road and the low μ road. However, in a high frequency band of 1 kHz or higher, the level when traveling on the low μ road is higher than that when traveling on the high μ road. For that reason, the level of the high frequency component of the output voltage of the vibration power generation element 11a serves as an index indicative of the road surface condition.

Therefore, the level of the high frequency component of the output voltage of the vibration power generation element 11a which is in the ground contact section is calculated by the level calculation unit 18, and the calculated level can be set as the road surface condition data. For example, the level of the high frequency component can be calculated by extracting the high frequency component from the output voltage of the vibration power generation element, and integrating the high frequency component extracted in the ground contact section.

Figure 7:
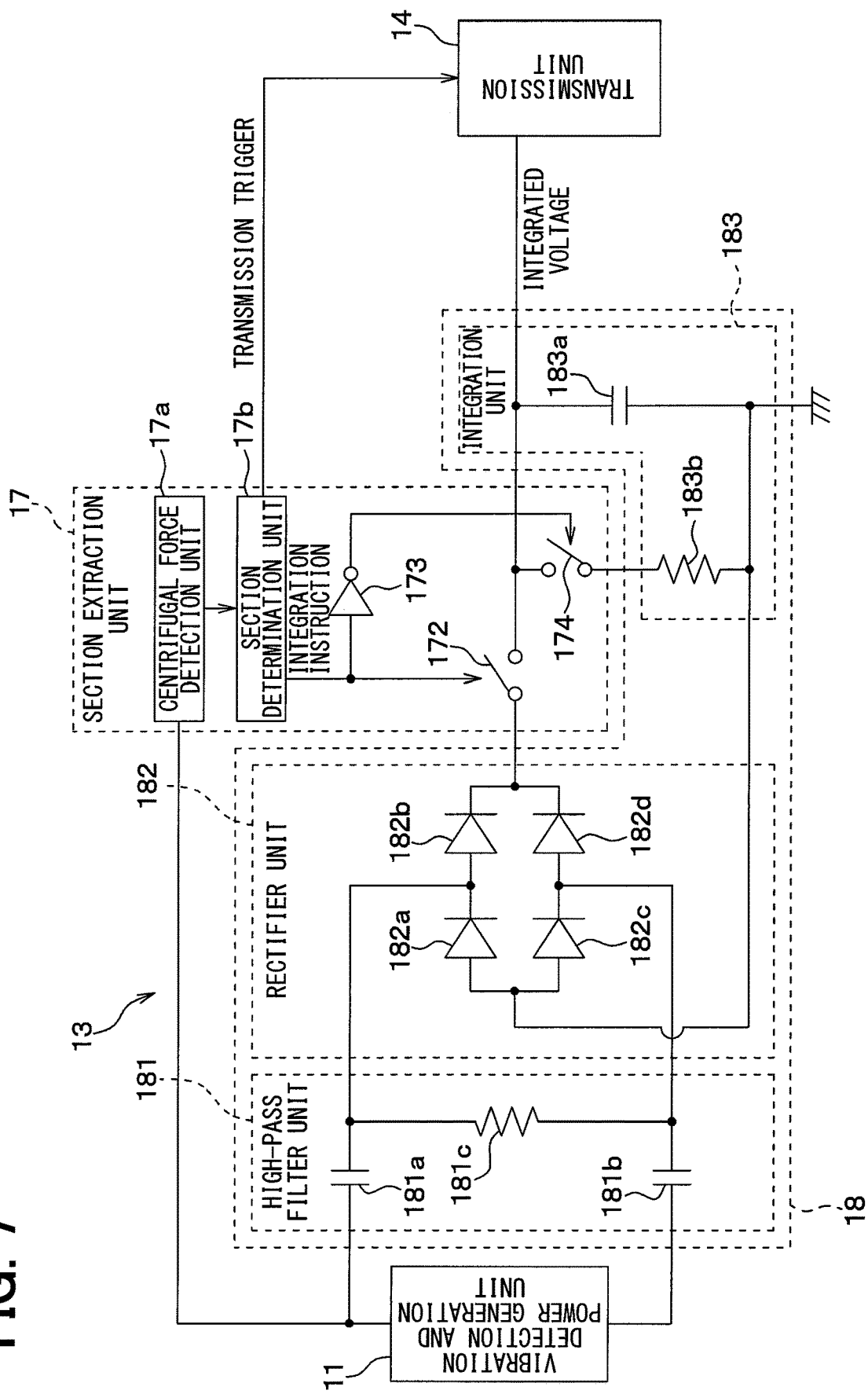
FIG. 7 is a diagram illustrating a specific circuit configuration of a processing circuit unit when a level of a high frequency component is calculated according to an integration of high frequency components extracted during the ground contact section.

FIG. 7 is a diagram illustrating a specific circuit configuration of the processing circuit unit 13 which is applied when calculating the level of the high frequency component according to the integration of the high frequency components extracted during the ground contact section of the vibration power generation element 11.

As described above, the section identification unit 17 includes a centrifugal force detection unit 17a and a section determination unit 17b, and the section determination unit 17b determines that the vibration detection and power generation unit 11 is in the ground contact section. The section determination unit 17b outputs an integration instruction signal at a start timing of the ground contact section and releases the integration instruction signal at an end timing of the ground contact section. In the present embodiment, when the high level is output as the integration instruction signal from the section determination unit 17b, a switch 172 turns on, and the high level is inverted by an inverter 173. Upon receiving the inverted low level, a switch 174 turns off, and the integration of the high frequency component starts. When the integration instruction signal is cancelled, and the output of the section determination unit 17b becomes low level, the switch 172 turns off, and the low level is inverted by the inverter 173. Upon receiving the inverted high level, the switch 174 turns on, and the integration of the high frequency component is terminated. In addition, the section determination unit 17b outputs a transmission trigger to the transmitter 14 at the end timing of the ground contact section.

The level calculation unit 18 includes a high-pass filter unit 181, a rectifier unit 182, and an integration unit 183.

The high-pass filter unit 181 is a high frequency component extraction unit that extracts the output voltage of the vibration detection and power generation unit 11, more specifically, the high frequency component of the detection signal of the vibration power generation element 11a. The high-pass filter unit 181 includes a CR filter circuit having capacitors 181a, 181b, and a resistor 181c, and passes only the high frequency component of the detection signal of the vibration power generation element 11a with the adjustment of a capacitance value of the capacitors 181a and 181b, and a resistance value of the resistor 181c.

The rectifier unit 182 includes a full-wave rectifier circuit having diodes 182a to 182d arranged in a bridge shape, and full-wave rectifies the high frequency component of the detection signal extracted by the high-pass filter unit 181. As a result, only a positive voltage that has been subjected to the full-wave rectification is applied to the integration unit 183.

The integration unit 183 integrates the high frequency component of the detection signal of the vibration power generation element 11a, and in the present embodiment, the integration unit 183 includes a capacitor 183a and a resistor 183b.

The capacitor 183a is charged based on the high frequency component that has been subjected to the full-wave rectification. A charging voltage of the capacitor 183a corresponds to a value obtained by integrating the high frequency components, and an integrated voltage value of the capacitor 183a is input to the transmitter 14 as data indicative of the road surface condition. In other words, as illustrated in FIG. 6, since the level of the high frequency component of the detection signal of the vibration power generation element 11a is different between a case where the traveling road surface is the low μ road surface and a case where the traveling road surface is the high μ road surface, the integrated voltage value of the capacitor 183a is changed according to the road surface condition.

Figure 8:
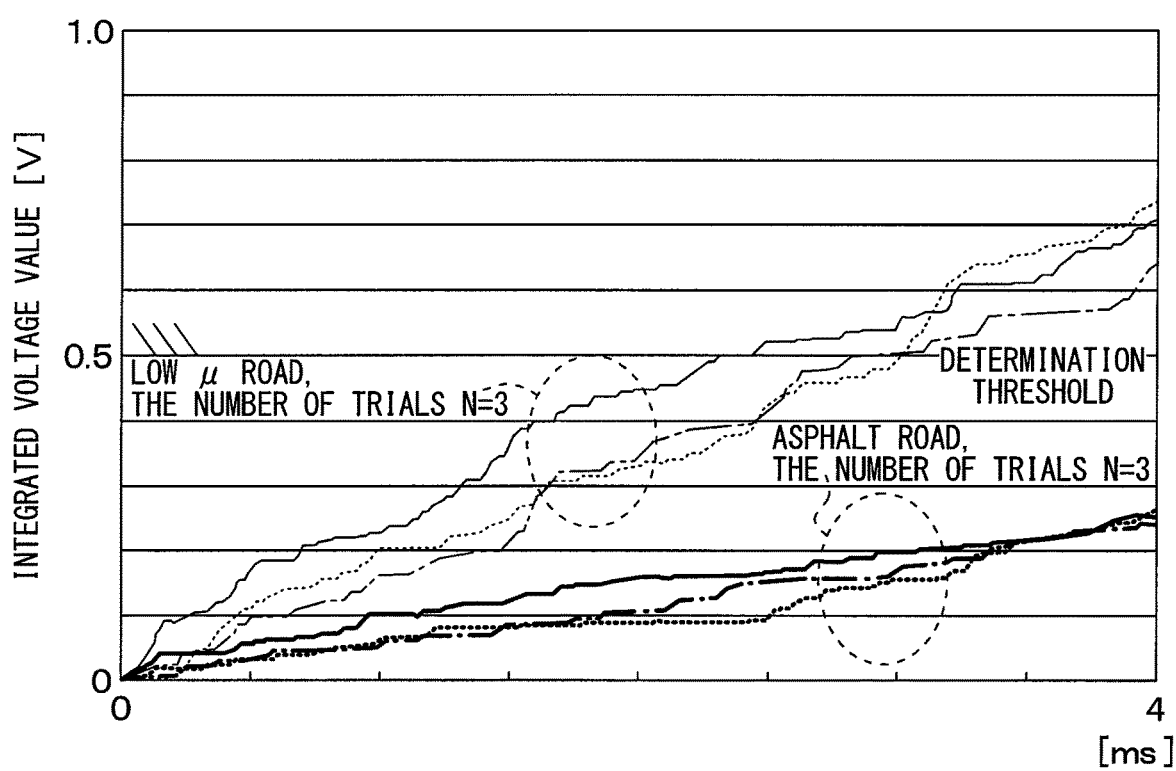
FIG. 8 is a graph showing a charging appearance in a capacitor in each of the case where the traveling road surface is the low μ road surface, and the case where the traveling road surface is the high μ road surface.

FIG. 8 shows a charging appearance in the capacitor 183a in each of the case where the traveling road surface is the low μ road surface, and the case where the traveling road surface is the high μ road surface, that is, the asphalt road. In each case, the charging operation is attempted three times, that is, the number of attempts N=3. As illustrated in the figure, when the traveling road surface is the low μ road surface, because the level of the high frequency component of the detection signal of the vibration power generation element 11a is larger than that in the high μ road surface, the integrated voltage value of the capacitor 183a becomes larger. As described above, because the magnitude of the integrated voltage value of the capacitor 183a is varied according to the road surface condition, the integrated voltage value of the capacitor 183a becomes data indicative of the road surface condition.

When the section determination unit 17b cancels the integration instruction signal to turn on the switch 174, the resistor 183b is connected to the capacitor 183a to discharge the capacitor 183a. As a result, when the high frequency component is then integrated, a voltage across the capacitor 183a can be reset to 0.

The processing circuit unit 13 can be implemented by the above circuit, and the high frequency component of the detection signal of the vibration power generation element 11a is integrated by the integration unit 183, thereby being capable of calculating the level of the high frequency component in a state where the vibration power generation element 11 is in the ground contact section.

The transmitter 14 transmits the road surface condition data transmitted from the processing circuit unit 13 to the vehicle side device 2. A communication between the transmitter 14 and a receiver 21 provided in the vehicle side device 2 can be implemented by a known short-range wireless communication technology such as Bluetooth (registered trademark). Any timing at which the road surface condition data is transmitted is applicable, but as described above, in the present embodiment, the transmission trigger is transmitted from the section determination unit 17b at the ground contact end time of the vibration detection and power generation unit 11 to transmit the road surface condition data from the transmitter 14. As described above, because the data transmission by the transmitter 14 is not always performed, but is performed exclusively at the ground contact end time of the vibration detection and power generation unit 11, the power consumption can be reduced.

The road surface condition data can be transmitted together with unique identification information (hereinafter referred to as "ID information") on a wheel provided for each tire 3 equipped in the vehicle in advance. Since a position of each wheel can be identified by a known wheel position detection device for detecting any position of the vehicle to which the wheel is attached, the road surface condition data is transmitted to the vehicle side device 2 together with the ID information, thereby being capable of discriminating which wheel the data is related to. Normally, it is assumed that the road surface $\mu$ of the traveling road surface is uniform. However, there is a $\mu$ split road different in the road surface $\mu$ between right and left wheels of the vehicle, and in such a $\mu$ sprit road, the road surface condition data is preferably transmitted for each wheel. It is needless to say that the road surface condition is not estimated for each wheel, but multiple road surface condition data may be used as the estimation of the road surface condition such that a mean value of the integrated voltage value indicated by the road surface condition data transmitted from each wheel is used for the estimation of the road surface condition.

On the other hand, the vehicle side device 2 is configured to include the receiver 21 and a condition estimation unit 22. The vehicle side device 2 receives the road surface condition data transmitted from the tire side device 1, and performs various processing based on the received data to detect the road surface condition during traveling.

The receiver 21 receives the road surface condition data transmitted by the tire side device 1. The road surface condition data received by the receiver 21 is sequentially output to the condition estimation unit 22 every time receiving the data.

The condition estimation unit 22 includes a known microcomputer having a CPU, a ROM, a RAM, an I/O, and so on, and performs processing for detecting the road surface condition according to a program stored in the ROM or the like. Specifically, the condition estimation unit 22 estimates the road surface $\mu$ based on the magnitude of the integrated voltage value indicated by the road surface condition data. For example, the road surface condition estimation unit 22 determines that the traveling road surface is the low $\mu$ road surface if the integrated voltage value is larger than a determination threshold, and the traveling road surface is the high $\mu$ road surface if the integrated voltage value is smaller than the determination threshold. As shown in FIG. 8, the determination threshold is set to an intermediate value between the integrated voltage value assumed when the traveling road surface is the low $\mu$ road surface and the integrated voltage value assumed when the traveling road surface is the high $\mu$ road surface. For that reason, the road surface condition of the traveling road surface can be estimated according to a comparison with the determination threshold.

When the road surface condition is estimated by the vehicle side device 2 as described above, the estimation result is communicated on, for example, a CAN (abbreviation of controller area network) that is a vehicle network. The estimation result of the road surface condition is input to, for example, an electronic control device for brake control, so-called brake ECU, and used for setting an index when performing an antilock brake control, for example, a control start threshold in the antilock brake control.

As described above, in order to detect the road surface condition, the road surface condition estimation device 100 according to the present embodiment extracts a detection signal of a portion that detects the vibration in the tire tangential direction in the vibration detection and power generation unit 11 which is in the ground contact section. Then, it is identified that the vibration detection and power generation portion 11 is in the ground contact section at that time based on whether the centrifugal force acting on the vibration detection and power generation unit 11 is generated, or not. Specifically, it is identified that the time when the centrifugal force is not generated is in the ground contact section. As a result, even if the pulse level of the output voltage of the vibration detection generation unit 11 changes according to the traveling speed of the vehicle, the ground contact section can be accurately identified. Therefore, the road surface condition can be accurately detected based on the ground contact section identified with high accuracy.

In addition, in the tire side device 1, the level of the high frequency component of the detection signal of the vibration in the tire tangential direction in the vibration detection and power generation unit 11 which is in the ground contact section is calculated, and the calculated level is transmitted as the road surface condition data. The road surface condition data is received by the vehicle side device 2 to estimate the road surface condition of the traveling road surface. As a result, the road surface condition can be estimated even without performing the frequency analysis, and the power consumption can be reduced while the number of frequency analysis components can be reduced. Therefore, the costs can be reduced.

In the processing circuit unit 13, the detection signal of the vibration in the tire tangential direction in the vibration detection and power generation unit 11 passes through the high-pass filter unit 181 to extract a high frequency component. In the processing circuit unit 13, after the extracted high frequency component has been rectified, the capacitor 183a is charged until the ground contact end time of the vibration detection and power generation unit 11 to obtain the integrated voltage value. In this way, because a portion of the processing circuit unit 13 except for the section determination unit 17b can be mainly implemented by an analog circuit, signal processing can be performed with a circuit of low costs and space saving. In addition, because the tire side device 1 may transmit the integrated voltage value caused by the capacitor 183a as the road surface condition data, the amount of transmission data from the tire side device 1 to the vehicle side device 2 can be remarkably reduced, and the power consumption can be more reduced. Therefore, the tire side device 1 can be downsized such that the vibration detection and power generation unit 11 provided in the tire side device 1 can be downsized, and mounting of the tire side device 1 into the tire 3 can be facilitated.

Second Embodiment

A second embodiment will be described. In the present embodiment, the configuration of the section identification unit 17 is changed as compared with the first embodiment, and other configurations are identical with those in the first embodiment. Therefore, only parts different from those in the first embodiment will be described.

Figure 9:
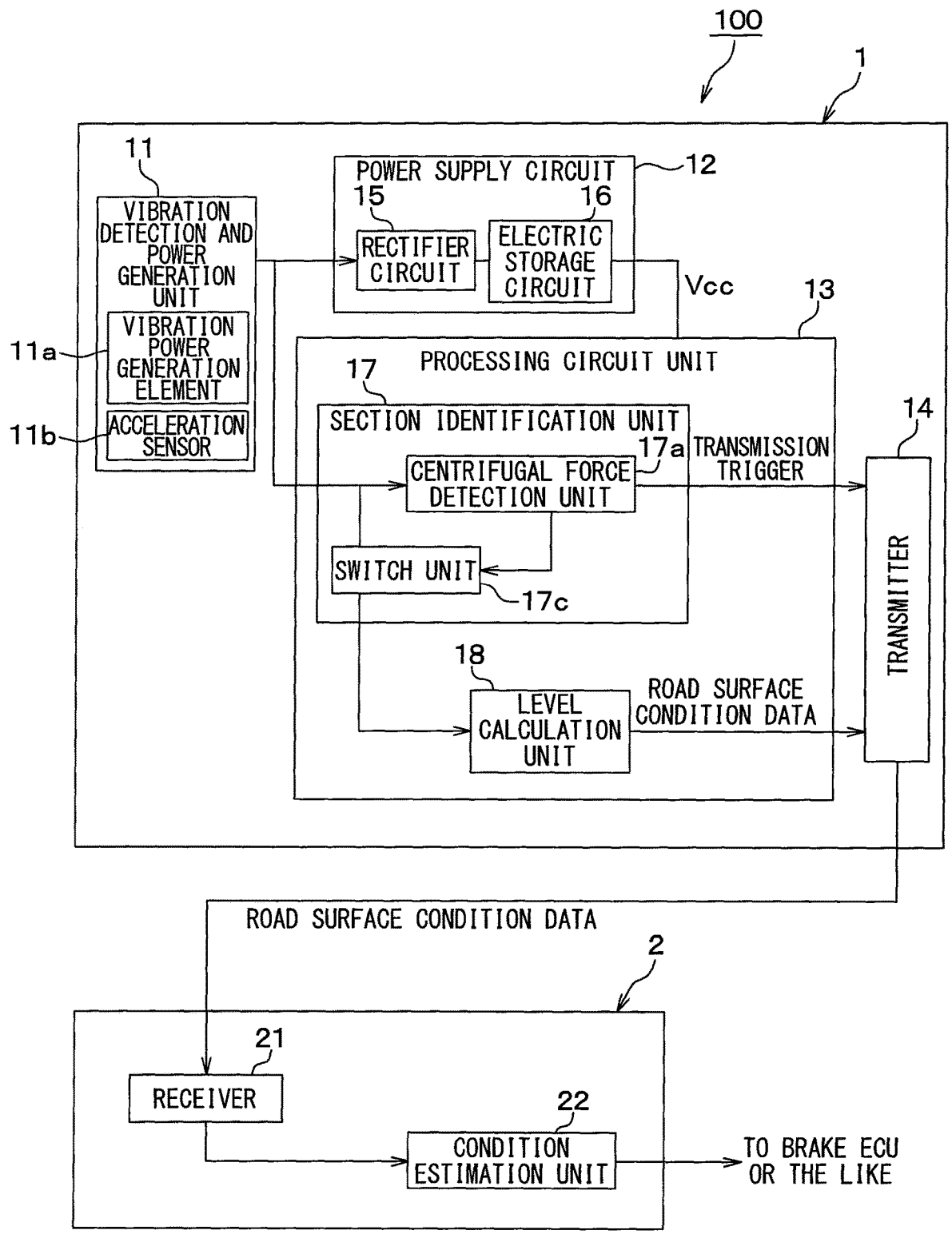
FIG. 9 is a diagram illustrating an overall block configuration of a road surface condition estimation device according to a second embodiment.

As shown in FIG. 9, in the present embodiment, a section identification unit 17 includes a centrifugal force detection unit 17a and a switch unit 17c.

As in the first embodiment, the centrifugal force detection unit 17a detects a centrifugal force acting on a vibration detection and power generation unit 11, but in the present embodiment, additionally, the on/off operation of the switch unit 17c is controlled based on the detected centrifugal force. Specifically, when the centrifugal force detection unit 17a determines that the centrifugal force acting on the vibration detection and power generation unit 11 is generated, the switch unit 17c is turned off, and when the centrifugal force detection unit 17a determines that no centrifugal force is generated, the switch unit 17c is turned on.

The switch unit 17c switches on and off an input of the detection signal of the vibration in the tire tangential direction from the vibration detection and power generation unit 11 to a signal processing unit 18. The switch unit 17c may be a semiconductor device or the like, or may be an analog switch. The detection signal of the vibration in the tire tangential direction from the vibration detection and power generation unit 11 is input to the signal processing section 18 when the switch unit 17c is turned on, and is not input to the signal processing unit 18 when the switch unit 17c is turned off. As described above, when the centrifugal force acting on the vibration detection and power generation unit 11, which is detected by the centrifugal force detection unit 17a, is 0, the switch unit 17c is turned on and the detection signal of the vibration in the tire tangential direction from the vibration detection and power generation unit 11 is input to the signal processing unit 18.

As described above, the section identification unit 17 can be provided with the switch unit 17c, and the switch unit 17c can be turned on when the centrifugal force acting on the vibration detection and power generation unit 11, which is detected by the centrifugal force detection unit 17a, is 0. Even with the above configuration, even if the pulse level of the output voltage of the vibration detection generation unit 11 changes according to the traveling speed of the vehicle, the ground contact section can be determined with high accuracy. Therefore, the detection signal of the vibration in the tire tangential direction from the vibration detection and power generation unit 11 can be input to the signal processing unit 18 only during the ground contact section based on the ground contact section determined with high accuracy. Therefore, the road surface condition can be detected with high accuracy.

It should be noted that the transmission trigger may be generated from the centrifugal force detection unit 17a. For example, when the centrifugal force detection unit 17a again detects the generation of the centrifugal force, the centrifugal force detection unit 17a may generate the transmission trigger. It is needless to say that as in the first embodiment, the section determination unit 17b may be provided so that the transmission trigger is generated from the section determination unit 17b.

Third Embodiment

A third embodiment will be described. In the present embodiment, a vibration detection and power generation unit 11 is provided with the same function as that of the switch unit 17c disposed in the section identification unit 17 in the second embodiment, and others are the same as those of the second embodiment. Therefore, only parts different from those in the second embodiment will be described.

Figure 10:
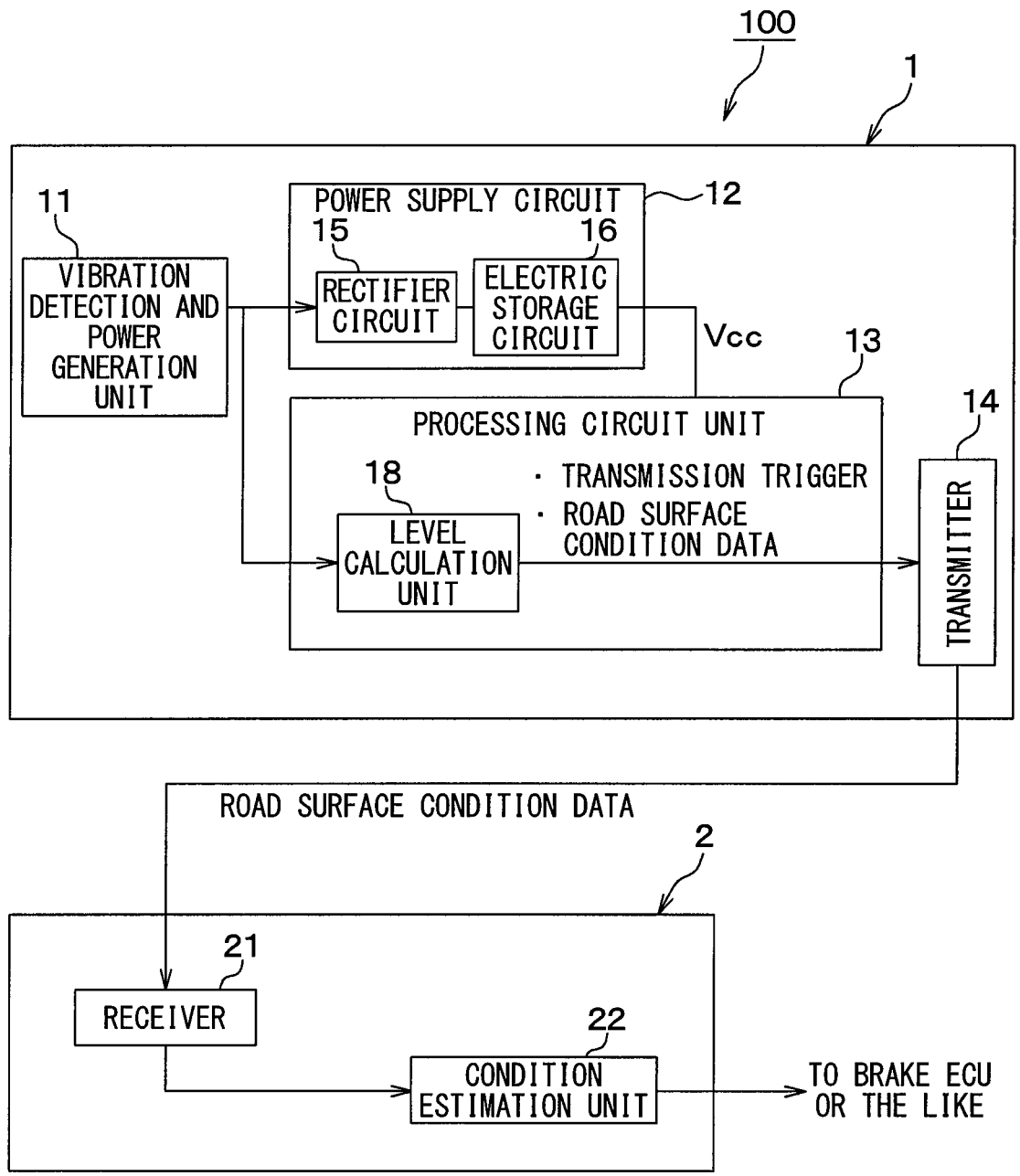
FIG. 10 is a diagram illustrating an overall block configuration of a road surface condition estimation device according to a third embodiment.

As shown in FIG. 10, in the present embodiment, a processing circuit unit 13 is formed by only a level calculation unit 18 so that a detection signal of the vibration detection and power generation unit 11 is input to the level calculation unit 18.

Further, in the present embodiment, the vibration detection and power generation unit 11 is configured as shown in FIG. 12. Specifically, the vibration detection and power generation unit 11 is configured to include a package 110, a sensor unit 111 having a beam portion 111a and a first weight portion 111b, a structure having a stopper portion 112 having a spring portion 112a and a second weight portion 112b.

The package 110 forms a hollow case, and has a back surface 110a, a side wall 110b, and an upper surface 110c on a side opposite to the back surface 110a. The back surface 110a of the package 110 is affixed to a back surface of a tread 31 of a tire 3 so that the vibration detection and power generation unit 11 is attached to the tire 3.

The sensor unit 111 is structured such that one end of the beam portion 111a is fixed to the back surface 110a of the package 110 and the first weight portion 111b is attached to the other end of the beam portion 111a. The first weight portion 111b moves according to the vibration in the tire tangential direction so that the beam portion 111a bends. A piezoelectric film not shown is formed on the beam portion 111a and electrodes are formed on both sides of the piezoelectric film. A potential difference based on a piezoelectric action of the piezoelectric film is generated between both of the electrodes according to the amount of bend of the beam portion 111a. The potential difference, that is, an output voltage is used as a detection signal corresponding to the vibration in the tire tangential direction from the vibration detection and power generation unit 11. Further, since the electricity can be stored in the power supply circuit 16 based on the output voltage, the vibration power generation element 11a can also be implemented by the sensor unit 111.

The stopper portion 112 switches on or off the detection of the vibration in the tire tangential direction by the sensor unit 111 based on the centrifugal force acting on the vibration detection and power generation unit 11. For that reason, the stopper portion 112 functions as the centrifugal force detection unit for detecting the centrifugal force acting on the vibration detection and power generation unit 11 described in the first and second embodiments. Specifically, the spring portion 112a and the second weight portion 112b are disposed on both sides of the sensor unit 111 in the tire tangential direction. As shown in FIG. 11, in a state in which no centrifugal force acts on the vibration detection and power generation unit 11, the second weight portion 112b is lifted toward the upper surface 110c by a restoring force of the spring portion 112a. As shown in FIG. 12, when the centrifugal force acts on the vibration detection and power generation unit 11, the second weight portion 112b is pulled toward the back surface 110a side against the restoring force of the spring portion 112a. As a result, the first weight portion 111b of the sensor unit 111 is clamped by the second weight portion 112b of the stopper portion 112.

In this way, in the state in which no centrifugal force acts on the vibration detection and power generation unit 11, the sensor unit 111 is released from the stopper portion 112 to detect the vibration. In the state in which the centrifugal force acts on the vibration detection and power generation portion 11, the sensor unit 111 is restrained by the stopper portion 112 so as not to detect the vibration.

With the use of the vibration detection and power generation unit 11 described above, the detection signal of the vibration detection and power generation unit 11 can be transmitted to the level calculation unit 18 in the processing circuit unit 13 only while the vibration detection and power generation unit 11 is in the ground contact section. Therefore, the vibration detection and power generation unit 11 can be structured to have the functions of the centrifugal force detection unit 17a and the switch unit 17c described in the second embodiment, and can have the same advantages as those in the second embodiment.

Furthermore, in the first and second embodiments, there is no need to provide the section identification unit 17 including the centrifugal force detection unit 17a and the like provided in the processing circuit unit 13. This makes it possible to reduce a processing load of the portion of the processing circuit unit 13 which is implemented by the microcomputer, and also makes it possible to reduce power consumption.

Modification Example of Third Embodiment

Figure 13:
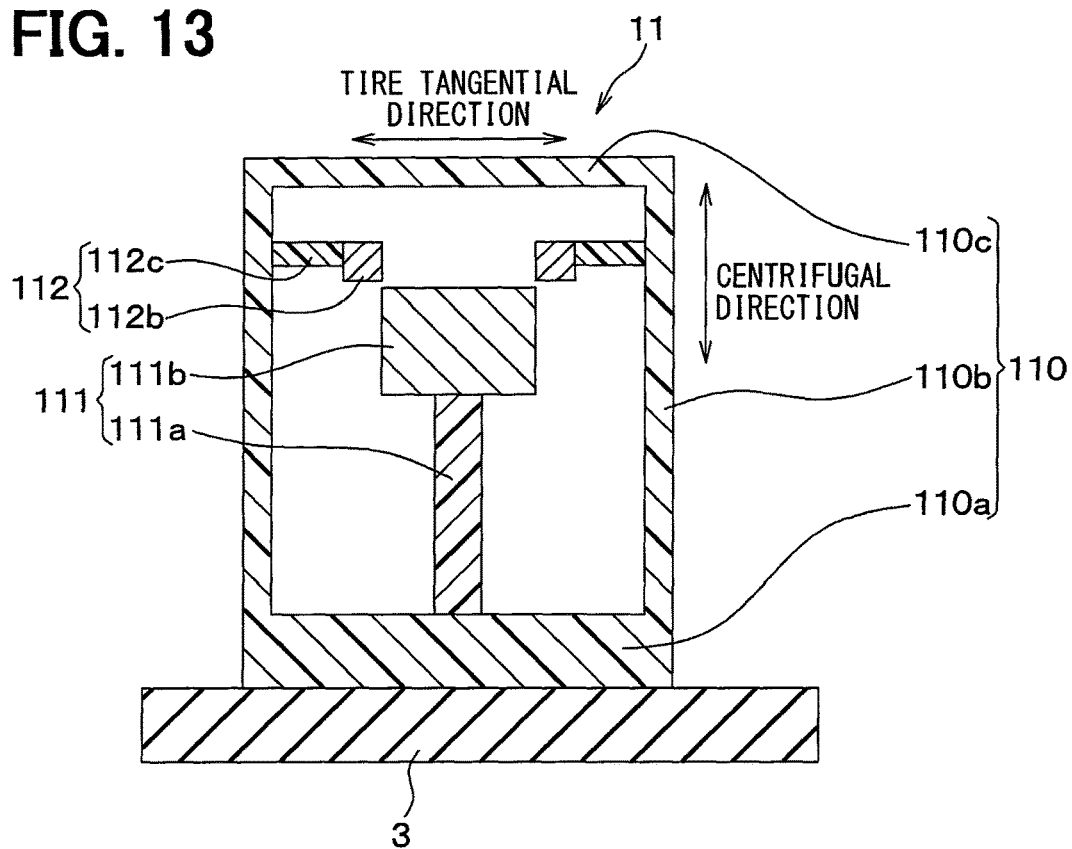
FIG. 13 is a cross-sectional view showing a state in which a centrifugal force of a vibration detection and power generation unit is not exerted according to a modification of the third embodiment.

As shown in FIG. 13, the configuration of the vibration detection and power generation unit 11 may be changed. Specifically, the stopper portion 112 is implemented as the second weight portion 112b and the beam portion 112c. One end of the beam portion 112c is attached to the side wall 110b of the package 110, and the second weight portion 112b is attached to the other end of the beam portion 112c.

Figure 14:
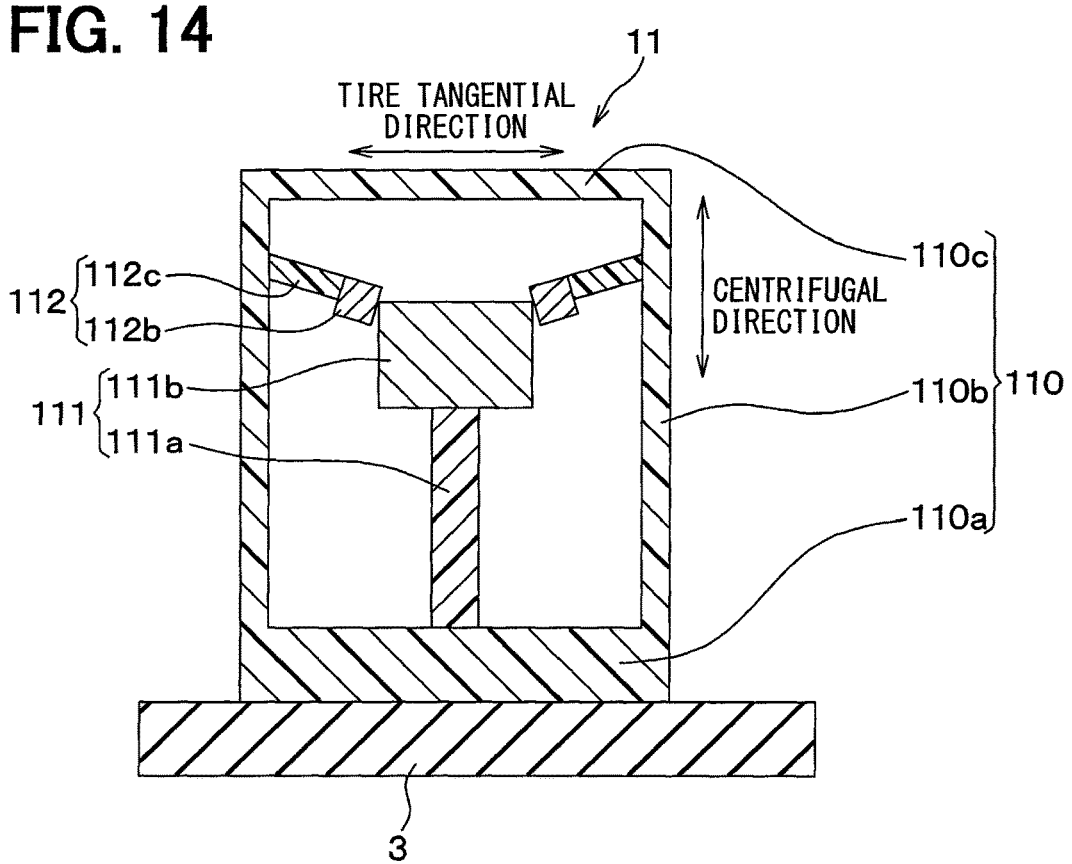
FIG. 14 is a cross-sectional view showing a state in which a centrifugal force of the vibration detection and power generation unit shown in FIG. 13 is exerted.

Even with the structure described above, in a state in which no centrifugal force acts on the vibration detection and power generation unit 11, the second weight portion 112b is lifted toward the upper surface 110c by a restoring force of the beam portion 112c. As shown in FIG. 14, when the centrifugal force acts on the vibration detection and power generation unit 11, the second weight portion 112b is pulled toward the back surface 110a side against the restoring force of the beam portion 112c. As a result, the first weight portion 111b of the sensor unit 111 is clamped by the second weight portion 112b of the stopper portion 112. Therefore, the present modification can also obtain the advantages described in the third embodiment.

Other Embodiments

Although the present disclosure has been described in accordance with the embodiments described above, the present disclosure is not limited to the above embodiments, but encompasses various modifications and modifications within the equivalent scope. In addition, it should be understood that various combinations or aspects, or other combinations or aspects, in which only one element, one or more elements, or one or less elements are added to the various combinations or aspects, also fall within the scope or technical idea of the present disclosure.

For example, in the above embodiment, the integrated voltage value transmitted from the tire side device 1 is compared with the constant determination threshold in the vehicle side device 2 to estimate the road surface condition. Alternatively, the determination threshold may be variable. For example, the vibration generated in the tire 3 is changed according to the vehicle speed, and the vibration generated in the tire 3 becomes larger as the vehicle speed is higher even in the same road surface condition. For that reason, the high frequency component included in the detection signal of the vibration detection and power generation unit 11 also becomes larger as the vehicle speed is larger, and the integrated voltage value charged in the capacitor 183a also becomes larger. Therefore, for example, the vehicle speed data is input to the condition estimation unit 22, and the determination threshold can be changed to a larger value as the vehicle speed indicated by the vehicle speed data is larger. The vehicle speed data calculated by a vehicle ECU, that is, an electronic control device for a vehicle based on the detection signal from, for example, a vehicle speed sensor or a wheel speed sensor may be acquired through a CAN communication.

Further, in the above embodiment, the section determination unit 17b extracts the high frequency component of the detection signal of the vibration power generation element 11a in a period of from the ground contact start time to the ground contact end time of the vibration detection and power generation unit 11, that is, during a ground contact time, and charges the capacitor 183a with the high frequency component to obtain the integrated voltage value. However, the above configuration is an example of the charging time when obtaining the integrated voltage value, and, for example, a constant time from the ground contact start of the vibration detection and power generation unit 11 may be set as a charging time when obtaining the integrated voltage value. For example, a time assumed as the ground contact time of the vibration detection and power generation unit 11 when the vehicle travels at a speed of 60 km/h can be set as the charging time. In that case, when the vehicle travels at the speed of 60 km/h or higher, a period during which the vibration detection and power generation unit 11 is located except for the ground contact section during the charging time is present, and the capacitor 183a is charged with the high frequency component of the detection signal of the vibration power generation element 11a even during that period. Therefore, in that case, it is preferable that the road surface condition estimation is not performed when the vehicle speed data is input, and the charging time exceeds the velocity speed assumed as the ground contact time of the vibration detection and power generation unit 11.

In the third embodiment, the portion detecting the centrifugal force in the vibration detection and power generation unit 11 is the stopper portion 112 provided in the vibration detection and power generation unit 11, and when the centrifugal force acts on the portion, the stopper portion 112 prevents the vibration in the tangential direction of the tire 3 from being detected. The same operation as that described above can be performed by providing the vibration detection and power generation unit 11 with a device that outputs a detection signal corresponding to the centrifugal force such as the acceleration sensor 11b. Specifically, the switch unit 17c as shown in the second embodiment is an analog switch and a switch control unit, and the detection signal corresponding to the centrifugal force from the vibration detection and power generation unit 11 is input to the switch control unit as a rectangular wave signal. Based on the rectangular wave signal, the switch control unit turns on the analog switch when the centrifugal force does not act, and turns off the analog switch when the centrifugal force acts. Even with the above manner, the same advantages as those in the third embodiment can be obtained.

Further, the switch unit 17c may be implemented as a semiconductor switching element, for example, a MOSFET, and the detection signal corresponding to the centrifugal force from the vibration detection and power generation unit 11 may be inverted directly or by an inverter or the like as the rectangular wave signal and applied as a gate voltage of the MOSFET. In this way, even with the configuration using the semiconductor switching element, the switch unit 17c can be turned on only when the centrifugal force does not act, and the same advantages as those in the third embodiment can be obtained.

What is claimed is:

1. A road surface condition estimation device provided in a vehicle, comprising:
    a tire side device that includes
        a vibration detection unit which is attached to a rear surface of a tread of a tire provided in the vehicle and which includes a portion detecting vibration in a tangential direction of the tire and a portion detecting a centrifugal force, the vibration detection unit configured to output a detection signal corresponding to a magnitude of the vibration in the tangential direction,
        a signal processing unit which includes a level calculation unit which calculates a level of a high frequency component of the detection signal, and
        a transmitter which transmits a calculation result of the level of the high frequency component as road surface condition data representing a road surface condition; and
    a vehicle side device that includes
        a receiver which receives the road surface condition data transmitted from the transmitter, and
        a condition estimation unit that estimates a road surface condition of a traveling road surface of the tire based on the road surface condition data, wherein
    the vibration detection unit is configured to not detect vibration in the tangential direction of the tire when the portion detecting the centrifugal force detects that the centrifugal force acts, and is configured to detect vibration in the tangential direction of the tire only when the portion detecting the centrifugal force detects that no centrifugal force acts.

2. The road surface condition estimation device according to claim 1, wherein
    the vibration detection unit comprises:
    a sensor unit that serves as the portion detecting the vibration in the tangential direction of the tire, the sensor unit including a first weight portion which is moved based on the vibration in the tangential direction of the tire and a beam portion attached to the first weight portion which bends according to movement of the first weight portion, the sensor unit configured to output the detection signal according to the bending of the beam portion; and
    a stopper portion that serves as the portion detecting the centrifugal force, the stopper portion including a second weight portion which is disposed on both sides of the first weight portion in the tangential direction of the tire and which moves based on the centrifugal force, wherein
    the stopper portion is configured to
        when the centrifugal force is acting on the stopper portion, hold the first weight portion with the second weight portion to restrain the first weight portion, and
        when the centrifugal force is not acting on the stopper portion, releases the first weight portion from the second weight portion.

* * * * *